United States Patent [19]

Reid

[11] 3,957,438

[45] May 18, 1976

[54] DETECTING FLUORITE IN A SOLID ROCK SAMPLE
[75] Inventor: Wilmot P. Reid, Golden, Colo.
[73] Assignee: Lost River Mining Corporation Limited, Toronto, Canada
[22] Filed: May 24, 1974
[21] Appl. No.: 472,954

[52] U.S. Cl. ................. 23/230 R; 23/230 EP
[51] Int. Cl.² ................. G01N 31/22; G01N 33/24
[58] Field of Search ................. 23/230 R, 230 EP

[56] References Cited
OTHER PUBLICATIONS

Schafer, "Application of Ion Exchange to Analysis of Phosphate Rocks," Anal. Chem., Vol. 35, No. 1, pp. 53–56, Jan. 1963.
Evans et al., "An Accurate and Rapid Method of Analysis for Fluorine in Phosphate Rocks" New Zealand J. Sci. Vol. 13, No. 1, pp. 143–148, Mar. 1970.
Hackh's Chemical Dictionary, 3rd Ed., p. 633, (1944).

*Primary Examiner*—Morris O. Wolk
*Assistant Examiner*—Barry I. Hollander
*Attorney, Agent, or Firm*—Fetherstonhaugh & Co.

[57] ABSTRACT

A method of detecting fluorite in an ore body comprising the steps of activating and dissociating the fluorite by the application of a cation exchange resin reagent, substituting the sodium ions of the activated and solubilized fluorite with a rare earth mineral and reacting the substituted rare earth mineral with an alizarin complexone to colour stain the fluorite whereby the presence of the fluorite may be readily detected.

3 Claims, No Drawings

DETECTING FLUORITE IN A SOLID ROCK SAMPLE

FIELD OF INVENTION

This invention relates to the detection of fluorite in an ore body. In particular this invention relates to a method of staining fluorite so that the presence of fluorite may be readily detected in an ore body.

PRIOR ART

Considerable difficulty has been experienced in attempting to detect the presence of fluorite by macroscopic inspection of drill cores where the ore body contains fluorite in fine veinlets. The detection of fluorite by macroscopic inspection is made difficult in specimens wherein the fluorite is present in small quantities because of the presence of other minerals of a similar chemical nature. A calculation of calcium fluoride based on total fluorine is very suspect because of the presence of other fluorine bearing minerals such as topaz or idocrase which may be present.

Because of the increase in value of fluorite it has become practical to mine reserves in remote areas even though the fluorite is present in relatively small quantities. One of the difficulties which is experienced in mining fluorite including minerals in remote areas is the difficulty of conducting a careful macroscopic examination. While it has been common practice to effect a colour sorting by staining minerals for a benification purpose or process, it has not previously been suggested to use a fluorite staining process for the purpose of identifying the fluorite in fine form in a gangue matrix. The present invention overcomes the difficulties of the prior art described above and provides a simple and inexpensive method of positively identifying fluorite in a mined specimen by means of a staining process.

PREFERRED EMBODIMENT

The present invention provides a simple and effective method of detecting fluorite in an ore body by means of a fluorite staining test that is based on the reaction of fluoride with a rare earth alizarin complexone (rare earth 1, 2-dihydroxyanthraquinon-3-ylmethylamine-N, N diacetic acid) to form a colored complex. A sodium-loaded cation exchange resin is used to activate the fluorite. Following this treatment, sodium of the activated fluorite is exchanged for lanthanum from a saturated lanthanum nitrate solution. A modified composite alizarin complexone, (i.e. less rare earth) reacts with a fluorite surface treated as described to form a purple complex which stains the fluorite surface.

According to an embodiment of the present invention there is provided a method of staining fluorite in a mineral sample comprising the steps of:
 a. activating and dissociating the fluorite by the application of a cation exchange resin reagent,
 b. substituting the sodium ions of the activated and solubilized fluorite with a rare earth mineral and thereafter reacting the substituted rare earth mineral with an alizarin complexone to colour stain the fluorite whereby the presence of fluorite may be readily detected.

The present invention also provides a reagent for activating and solubilizing fluorite consisting of a sodium cation exchange resin.

According to a further embodiment of the invention the fluorite staining solution is in the form of a rare earth alizarin complexone having the formula, rare earth 1, 2-dihydroxyanthraquinon-3-ylmethyl-amine-N, N-diacetate acid.

The invention will be more clearly understood after reference to the following specific examples:

EXAMPLE I

An alizarin complexone (AC) stock solution was prepared containing:
 0.0167 M alizarin fluorine blue [$C_{19}H_{15}NO_8 \cdot 2H_2O$]
 0.125 ml $NH_4(OH)_2$
 0.25 ml glacial acetic acid.

A lanthanum nitrate stock solution was prepared consisting of:
 1/60 M lanthanum nitrate.

A buffer solution was prepared as follows:
 60 g sodium acetate trihydrate were dissolved in 500 ml $H_2O$,
 115 ml glacial acetic acid were added and diluted to 1 liter.

Reagent I

A composite fluoride reagent was prepared consisting of:
 330 ml acetone
 68 ml of buffer solution
 10 ml AC solution
 75 ml $H_2O$,
was warmed to room temperature and diluted to 500 ml with $H_2O$. It was found that this reagent could be conveniently stored in polyethylene bottles and was good for a period of 5 days.

Fluorite Staining Test No. 1

A test sample in the form of a core sample known to contain fluorite veinlets was immersed in a mixture of sodium-loaded cation exchange resin and water in the ratio of 1/10 for 30 minutes. The exchange resin activates and dissociates the fluorite mineral. The removal of calcium ion for sodium causes a shift in the equilibrium of the equation listed below.

$$CaF_2 \rightleftarrows Ca^{+2} + 2F^{-1}$$

The activated and dissociated sample was then ready for the next treatment step. In this step the sample is first rinsed lightly and then placed in a saturated lanthanum nitrate solution for ½ hour. The pH is adjusted to 6 with ammonium acetate. It is necessary to substitute the sodium with lanthanum because it is the lanthanum to which the dye complex bonds to and gives the fluorite its characteristic staining colour.

The final step is to rinse the lanthanum substituted fluorite lightly and blot to dryness and then place the test sample in a composite alizarin complexone solution, reagent I above.

After the sample was removed from the alizarin complexone reagent solution the fluorite present in the sample was found to be stained a pale purple and was clearly recognizable.

EXAMPLE II

A test sample similar to that used in Example I was immersed in a mixture containing a sodium-loaded cation exchange resin and water (1/10) ratio for 2 hours. The sample was then rinsed lightly and placed in a saturated lanthanum nitrate for two hours. The sample was then rinsed lightly and placed in 100 ml. composite reagent No. 1 for 30 minutes. After the sample was removed from the AC reagent No. 1 it was found to be stained purple.

EXAMPLE III

A sample sq gr>2.90<3.3 fraction of Lost River composite was used for the purpose of this test. 1g of the sample was immersed in a mixture of ion exchange resins and water (1/10) ratio for 3 hours. The resins were removed and the sample was placed in 20 ml 1N lanthanum nitrate for 2 hours in a shaker. The sample was then washed lightly, dried and covered with 5 ml composite reagent I for 1 hour. After the sample was removed from the alizarin complexone reagent solution the fluorite present in the sample was found to be stained violet and was clearly distinguishable.

Numerous other tests were carried out including a test using the rare earth metal cerium. It was found that the cerium provided a light violet colour stain which was not as clearly distinguishable as the lanthanum and was, therefore, not satisfactory for the purpose of the present invention.

EXAMPLE IV

A sample consisting of plus 65M fluorite weighing about 1 gram was immersed in 5 ml of 1N EDTA (ethylenediamine tetra acetic acid) for 1 minute. The sample was then washed lightly and placed in a 5 ml composite reagent No. 2 for 1 minute. The test sample was not stained by this procedure. The composite fluorite reagent No. 2 consisted of the following:

330 ml acetone
68 ml of buffer solution
10 ml AC solution
10 ml Lanthanum nitrate-solution
75 ml $H_2O$ This reagent was warmed to room temperature and diluted to 500 ml in $H_2O$.

EXAMPLE V

A sample, the same as that tested in Example IV, was immersed in a mixture containing 5 ml 1N EDTA and 5 ml composite reagent No. 2. The test was observed under a binocular for 3 minutes and the staining effects were negative.

From a total of 68 staining tests which were conducted using a variety of reagents and procedures, however, the only tests to give satisfactory results are those described above in Examples I, II and III.

From the foregoing we find that the present invention provides a simple and efficient method of staining fluorite so that the presence of fluorite can be detected in an ore body. The method of the present invention is capable of use in remote mining areas and serves to identify fluorite present in narrow veinlets. One of the major applications of the present invention is the use of the method in the field during exploratory diamond drilling operations where it is very often extremely difficult to detect the presence of fluorite in diamond drill core. The difficulties experienced in detecting the presence of fluorite in diamond drill core are expected to increase as the higher grade deposits are worked out and those of the fine grained disseminated or veinlet macroscopic type are being evaluated. These and other advantages of the present invention will be apparent to those skilled in the art.

What I claim as my invention is:

1. A method of detecting the presence of fluorite in a solid rock sample comprising the steps of:
   a. activating and solubilizing only the surface fluorite by applying to the surface of the rock sample a sodium cation exchange resin reagent,
   b. substituting the sodium ions of the NaF of the activated and solubilized fluorite with a rare earth element,
   c. reacting the thus obtained rare earth fluoride with an alizarin complexone to colour stain the rock at the site of the solubilized fluorite whereby the presence of the fluorite is readily detected.

2. A method as claimed in claim 1 wherein the rare earth element is lanthanum.

3. A method as claimed in claim 1 wherein the fluorite staining solution is in the form of a rare earth alizarin complexone having the formula rare earth 1, 2-dihydroxyanthranquinon-3-ylmethyl-amine-N, N-diacetate.

* * * * *